United States Patent [19]

Fukunaga

[11] 4,265,235

[45] May 5, 1981

[54] ANESTHETIC SYSTEM

[76] Inventor: Atsuo F. Fukunaga, 13139 Bryson St., Arleta, Calif. 91331

[21] Appl. No.: 38,319

[22] Filed: May 11, 1979

[51] Int. Cl.³ ............................................. A61M 16/00
[52] U.S. Cl. ........................... 128/200.24; 128/205.12; 128/205.17; 128/911; 138/114
[58] Field of Search ..................... 128/201.11, 205.12, 128/205.17, 200.18, 204.25, 204.18, 204.26, 206.15, 205.24, 205.18, 203.26, 204.22, 911; 138/114

[56] References Cited

U.S. PATENT DOCUMENTS

| | | | |
|---|---|---|---|
| 2,875,756 | 3/1959 | Gagnan | 128/911 |
| 4,188,946 | 2/1980 | Watson et al. | 128/911 |

FOREIGN PATENT DOCUMENTS 93941  8/1923  Austria ...................... 128/911

Primary Examiner—Henry J. Recla
Attorney, Agent, or Firm—Cislo & O'Reilly

[57] ABSTRACT

This application discloses a unilimb device of universal application to different types of breathing systems. The device comprises two gas carrying tubes, one within the other, the corresponding ends of the tubes being within two common terminal elements. One of the terminal elements provides for two separate passages, each being connectable, one to a source of gas, and the other for disposition of the expiratory gases. The other terminal element includes a nozzle end for connection to the inlet for the patient's respiratory system, with the opposite end serving to receive the other ends of the two flexible tubes and to provide short passages to the nozzle to minimize dead air space. Provision may be made for telescoping each terminal element, and the inlet element may be provided with a member for extending or adapting it to different breathing systems.

9 Claims, 25 Drawing Figures

Fig.4e,f

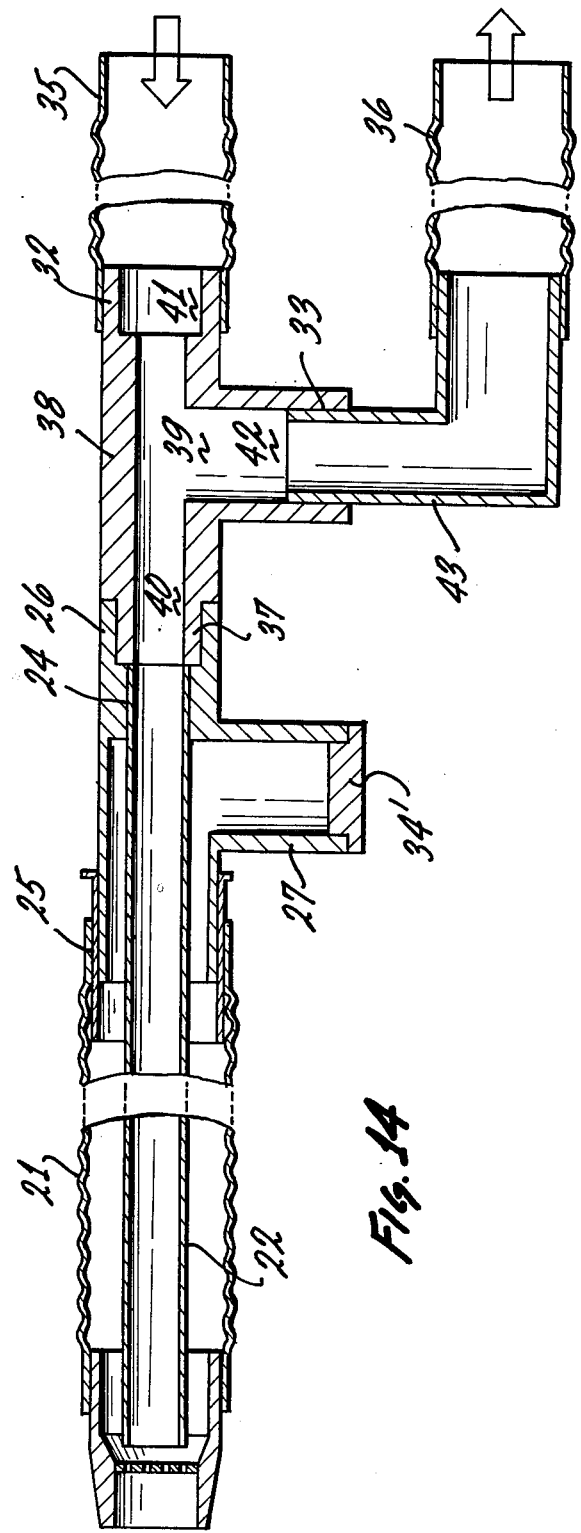
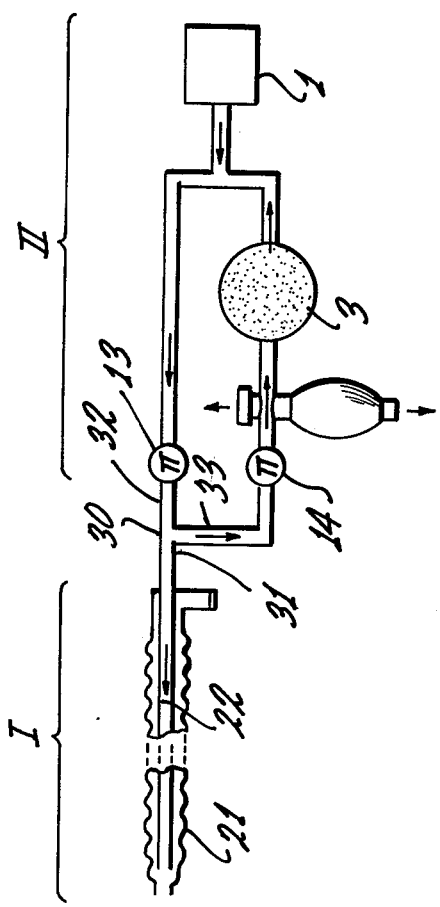
Fig. 14
Fig. 15

ANESTHETIC SYSTEM

CROSS-REFERENCE TO RELATED APPLICATION

This application corresponds to the disclosures of two Japanese applications viz No. 53-057593, filed May 17, 1978 and Oct. 13, 1978, the priority dates of which application applicant claims under the International Convention.

BACKGROUND OF THE INVENTION

The present invention relates to devices utilizable in different types of breathing systems, such as those for administering anesthetic gases, or for the administration of oxygen to patients.

In recent years a number of improvements have been evolved for use in the practice of inhalation anesthetic administration. These improvements include: the two tube circle circuit disclosed in U.S. Pat. No. 3,556,097; the unilimb device and the anesthesia breathing system disclosed in U.S. Pat. No. 4,007,737; the anesthetic system described in the article entitled "A Streamlined Anesthetic System" J. A. Bain and W. E. Sporel, which appears in Volume 19, No. 4 at page 426 of the Canadian Anesthetic Society Journal (July 1972), and the tube device of which is disclosed in U.S. Pat. No. 3,856,051 granted Dec. 24, 1974; and the system described by Drs. S. Ramanathan, Chalon, and Turndorf in an article entitled "A Compact, Well-Humidified Breathing Circuit For the Circle System" which appeared in Volume 44, No. 3 commencing at page 238 of the March 1976 issue of Anesthesiology.

Among such and other well-known breathing systems, that most commonly used is probably the circle circuit, orginally introduced in 1926 and an improvement of which is disclosed in U.S. Pat. No. 3,556,097 mentioned above. The principal problem in utilizing a circle circuit of such design arises from the use of two flexible tubes. Such tubes can impede the surgeon who may be confronted with having to operate in the vicinity of the head and neck of the patient. In addition, the same sized flexible tubes used in a circuit system for adults, cannot be employed for infants. Instead a miniaturized pair of flexible tubes must be utilized for the latter. While the rebreathing system described by Drs. Bain and Sporel in the article, and his pipe disclosed in said U.S. Pat. No. 3,856,051, mentioned above, have certain advantages from the standpoint of ease in the application to the patient and handling, the particular circuit is not generally regarded as efficient with regard to fresh gas economics during spontaneous breathing. Nor would the fresh gas tube of the said patent support such breathing. This pipe is, therefore, limited in its usage to the Bain and Sporel rebreathing system which has not been generally accepted to replace the circle circuit system.

In an effort to overcome the physical problems presented by the use of two flexible tubes or hoses in the manner illustrated in U.S. Pat. No. 3,556,097, both the patentee of U.S. Pat. No. 4,007,737 and Drs. Ramanathan, Chalon, and Turndorf have illustrated and described unilimb devices utilizable in a circle circuit system.

Although the unilimb devices thus suggested by prior researchers in this field have offered advantages over the two tube or hose system previously used in a circle circuit system, there are certain critical aspects in such prior unilimb devices which can present problems in certain applications therefor and/or which may otherwise limit their use to special situations. For example, although the unilimb of U.S. Pat. No. 4,007,737 is designed to minimize dead air space in a circle circuit breathing system, it does so by providing two one way valves in the terminal connector adapted for attachment to the mouth piece or other inlet means to the patient's respiratory system. Since any malfunction of either one-way valve could have a most serious, if not fatal, consequence, it becomes highly desireable to eliminate such valves altogether in this location. Further, by providing spacers between the inner and outer tubes in order to maintain them in a concentric disposition, the unilimb of the last-mentioned patent can develop undesireable gas flow impediments when the tubes become twisted.

While the clinical report by Drs. Ramanathan et al. does illustrate the use of a unilimb flexible tube or hose system between the source of the gas and the patient, insufficient details of the patient end of the device are disclosed to enable one skilled in the art to determine its exact physical structure.

Prior art devices of these types, moreover, appear to have been designed and utilizable only for particular applications. Thus, for example, a unilimb device for a circle circuit has had no utility in the rebreathing system described by Drs. Bain and Sporel in the article heretofore referenced. conversely, no device specifically designed for use in a rebreathing system, has heretofore been employable in a circle circuit system.

Additionally, prior art devices have been structured for a particular application and with fixed physical characteristics e.g. to provide a predetermined volume of dead air space, thus limiting the use of the device to the specific application for which the device may have been designed. Hence, if, for example, it should become desireable in the circle circuit to provide more or less dead air space than a given unilimb device is designed to provide, it has been necessary heretofore to have a new unilimb device designed and fabricated for such other specific application.

It has also been the observation of the present inventor that such unilimb prior art devices as have heretofore been described in any of the references, such as those hereinabove mentioned, have not been found particularly practicable from the standpoint of being readily manufacturable at a reasonable cost. This would appear to be particularly the situation with respect to the device of U.S. Pat. No. 4,007,737 with its one-way valve system and spacers for maintaining concentric disposition of the inner tube with respect to the outer tube.

If the cost of manufacturing such devices should prove too great, there will be considerable reluctance on the part of hospitals and other potential users of the devices to purchase the same, and particularly to discard them where such discard might become necessary or desireable after use with a patient which may have some type of communicable disease. Prior unilimb devices moreover have not heretofore been constructed in such a manner as to be easily disassemblable for cleaning sterilization or other type of servicing.

Thus, the devices of the prior art have not proved to be satisfactory from the standpoints of their fabrication, their servicing, their disposability, their utility, nor their adaptability for use in different systems, or for different applications in the same system.

SUMMARY OF THE INVENTION

The present invention will be found to provide a unilimb device which may be easily and inexpensively fabricated for assembly or dissassembly, and hence, is readily servicable. It may be constructed for adaptation to universal applications, not only to satisfy different requirements for gas handling in the same system, but for use in both the circle circuit system and the rebreathing system.

The invention comprises a pair of flexible gas conducting tubes, one being of a smaller diameter than the other and serving to conduct the inspiratory gas from a source thereof inlet means for the patient's respiratory system. The larger flexible tube is disposed about the smaller tube and, through the space between the two tubes, may serve to conduct expiratory gas from such inlet means back to a carbon dioxide absorber, or for other disposition. The two tubes extend between a pair of more rigid plastic terminals. One of such terminals may be provided with outer and inner tubular extensions to which one of the pair of corresponding ends of the larger and smaller tubes maybe attached respectively, with the smaller tubular extension, placing the smaller tube in communication through an opening in the terminal with a hose from inspiratory gas source; and with the terminal providing a separate gas passage whereby the larger tubular member may be placed, through another opening in the terminal, in communication with a hose leading to the $CO_2$ absorber or other unit.

The other terminal may be short and tubular in configuration, having one end adapted for connection with the inlet means for the patient's respiratory system, and its other end adapted to receive the other ends of the two flexible tubes. The end of the larger tube may grippingly fit over or inside the other terminal end, and the end of the smaller tube may extend therein. An orificed transverse wall may be disposed between the two terminal ends and serve as a stop for the axial advance of the end of the smaller tube, thereby to prevent the inner tube from obstructing the flow of expiratory air back through the larger tube. Because of the proximity of the end of the smaller tube to the inlet means the amount of dead space in the vicinity of the inlet means to the patient's respiratory system, may be minimized. The open ends of both the larger and smaller flexible tubes are in direct communication with the nozzle leading to the inlet means to the patient's respiratory system, as well as with each other. Since the pressure of the gas arriving through the smaller tube will always be in excess of the pressure of the gas being carried away by the larger tube, and because the one-way valves are already provided by the anesthesia machine, no one-way valve has been found to be necessary at the outlet of the inner tube, or the entrance of the outer tube. Even when the patient exhales back through the nozzle, the expiratory gas will be carried away between the walls of the larger and smaller tubes.

While the device in a circle circuit system thus provides a minimum of dead space, a requirement particularly important in the administration of oxygen to infants, it is also part of the present invention to provide telescoping or adapter elements for either or both of the terminals whereby, paradoxically, dead space may be increased for situations where the level of the carbon dioxide in a patient may become abnormally low, as for example, where patients may be receiving prolonged artificial ventilation. by sliding out the telescoping tubular extensions, the circuit may readily be adapted to provide adequate dead space to enable the patient's carbon dioxide level to be regulated over a wide range, thereby facilitating the maintenance of normocapnia during anesthesia and mechanical ventilation, when appropriate.

It is also a feature of the present invention that the second terminal, which may normally be connected to the source of gas, and the carbon dioxide absorber, may be modified in a number of ways by the use of a plug and an adapter, to increase dead space in a circle circuit. Additionally, by connecting a bag or a respirator, or a one-way valve, to the opening in the terminal which would normally be in communication with a carbon dioxide absorber in a circle circuit system, the device may be adapted to a rebreathing or non-rebreathing circuit for use in transporting a patient away from an operating room during recovery or when adequate anesthetic machines are not readily available.

Because the components of the device of the present invention are relatively simple to construct and may be manufactured as separate items, they may be easily assembled into the complete unilimb device, and any one of the components may be quickly replaced should such replacement become necessary. Additionally, since the several components may be readily detached from the other components, each of the components may be easily cleaned and sterilized. Also, because the cost of fabricating the several components is not great, any or all of the components may be simply be disposed of after any use thereof, as for example, by a patient having a contagious disease or a communicable virus.

While it is contemplated that the inner tube shall be used as the inspiratory limb, and the outer tube as the expiratory limb in order to avoid obstruction due to water condensation of the exhaled gases which may occur after prolonged artificial ventilation, it would be possible to reverse the connections without hypercarbia and hypoxia presenting immediate hazards to the patient.

The device of the present invention may thus be adapted for use in any of the several presently used breathing systems in order to utilize the most desirable features of such circuit for any particular application. In other words, the same unilimb device may be utilized either in a circle circuit, or as a re-breathing circuit, or a non-rebreathing circuit, a pediatric circuit with a minimum dead space, or to provide greatly augmented dead space in any of such circuits to regulate arterial carbon dioxide. Moreover, the device has proven to be extremely reliable and affords safe institution of spontaneous, assisted or controlled ventilation. This results particularly from the elimination of valves in the terminal and the need for maintaining concentricity of the tubes by spacers or other means.

BRIEF DESCRIPTION OF THE DRAWINGS

In the accompanying drawings:

FIG. 4(e) is a section on the line e—e of FIG. 3;
FIG. 4(f) is a section on the line f—f of FIG. 3;
FIG. 14 is a longitudinal section similar to FIG. 3, but illustrating a modification of, and addition to, the terminal shown on the right-hand side of FIG. 3;
FIG. 15 is a schematic view of the circuit in which the embodiment of the invention illustrated in the FIG. 14 may be utilized.

DESCRIPTION OF THE PREFERRED EMBODIMENTS

Figure 1:
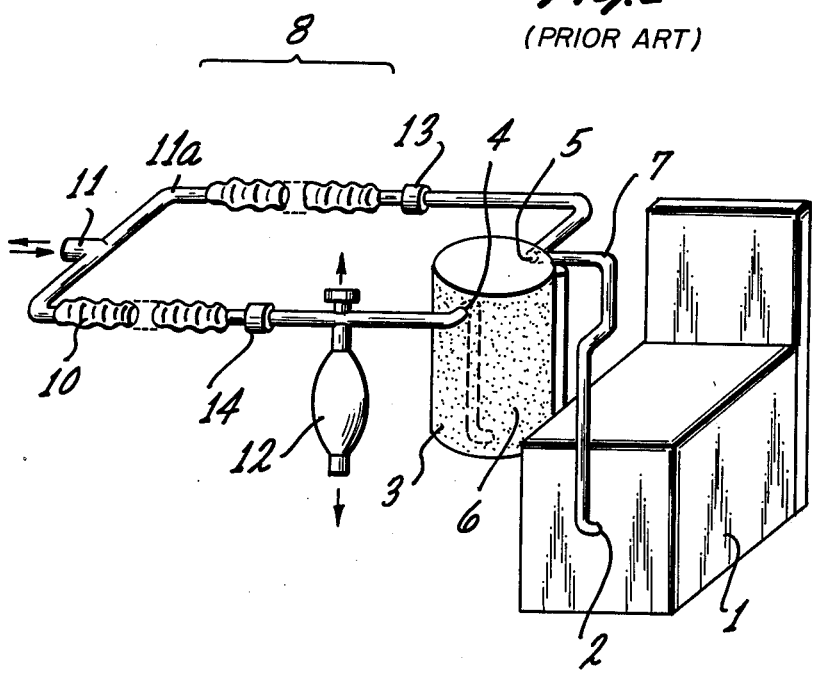
FIG. 1 illustrates, in perspective view, a typical conventional dual tube circle circuit.

Referring to FIG. 1 of the drawings, a typical circle circuit includes a source of gas 1, conduit means 2 extending therefrom, and a carbon dioxide absorber 3 which receives exiratory gas through a conduit 4. Reprocessed gas moves out through the outlet 5 after having passed through the carbon dioxide absorbing granule 6. As the reprocessed gas moves out of the outlet 5, it joins fresh gas from the source 1 as the fresh gas is arriving through the conduit 7, and the merged gases then pass through the one-way inspiratory valve 13 and the flexible hose 9 into the common inlet-outlet pipe 11, as inspiratory gas to the inlet means (not shown) to the patient's respiratory system. The expiratory gases return through the inlet pipe 11, but then pass back through the return hose 10, one-way expiratory valve 14, past the reservoir bag 12 and into the carbon dioxide absorber 3 through the inlet for reprocessing. This system is shown schematically in FIG. 2.

Figure 2:
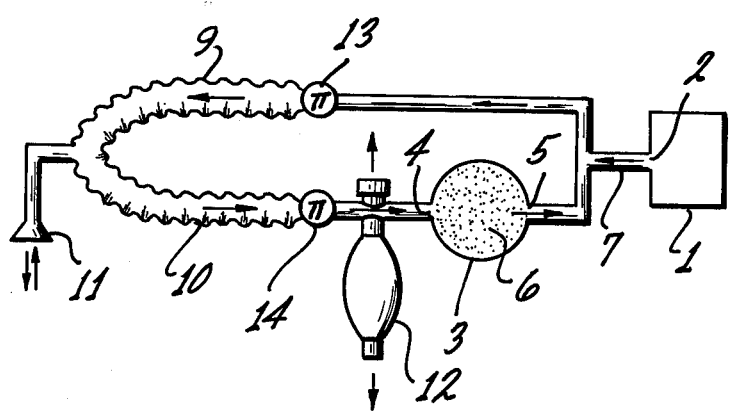
FIG. 2 is a schematic view of the circle circuit of FIG. 1.

The device of the present invention is intended to replace the two hoses 9 and 10, and the inlet-outlet pipe 11 of the circle circuit thus illustrated in FIGS. 1 and 2, and briefly described above. The inspiratory tube 22 is extended through the expiratory tube 21. The difference in the diameters of these two tubes is such that a sufficient volume of expiratory air may pass between the outer wall of the inner tube 22 and the inner wall of the outer tube 21. The latter desirably may be constructed of plastic, as a corrugated tube, while the inner tube 22 preferably is extruded of a vinyl type material. These two tubes are separately fabricated, so that when the device of the present invention is to best assembled, the smaller tube 22 is simply pushed in and through the outer tube 21 until the leading end of the tube 22 appears at the other end of the corrugated outer tube 21.

Figure 3:
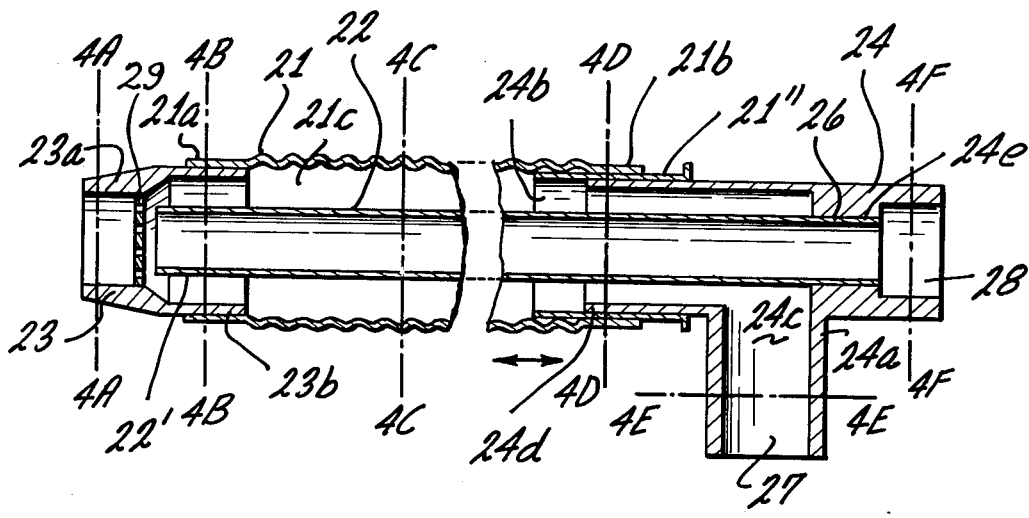
FIG. 3 is a longitudinal cross-section of the preferred embodiment of the device of the present invention.
Figure 4A:
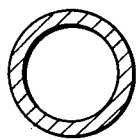
FIG. 4(a) is a section on the line a—a of FIG. 3.
Figure 4B:
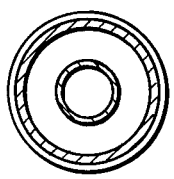
FIG. 4(b) is a section on the line b—b of FIG. 3.
Figure 4C:
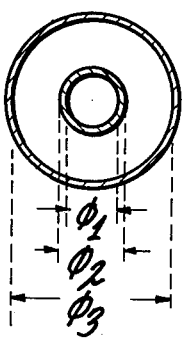
FIG. 4(c) is a section on the line c—c of FIG. 3.
Figure 4D:
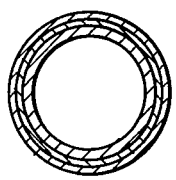
FIG. 4(d) is a section through the line d—d of FIG. 3.

As may be seen in FIG. 3, two corresponding ends 22' and 21a of the inner tube 22 and outer tube 21 are disposed in and about a terminal element 23, respectively. This element 23 may be generally tubular in configuration, with a tapered nozzle end 23a for connection with the inlet means to the patient's respiratory system. The external diameter of the opposite cylindrical end 23b of the terminal element 23 is such as to enable the uncorrugated end 21a of the tube 21 to be force fitted thereover. A transverse wall 29, preferably orificed in the manner shown in FIG. 5, with the orifices 29', may serve as a stop to prevent the end 22' of the tube 22 from extending into the opening in the nozzle end portion 23a of the terminal element 23 and thereby block the flow of expiratory air back into the expiratory air passage 21c, but permitting such end 22' to be disposed as close as possible to the opening in the nozzle end portion 23a.

Figure 6:
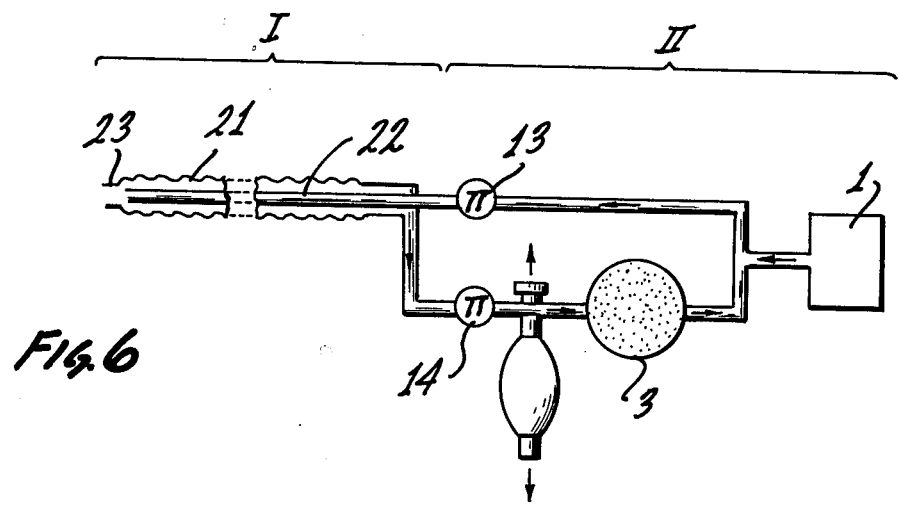
FIG. 6 is a schematic view of a circle circuit of FIG. 2 in which the device of FIG. 3 has been substituted for the two hose arrangement of FIGS. 1 and 2.

The opposite ends 21b and 26 of the tubes 21 and 22 respectively, are connected to a second terminal element 24. This second terminal element 24, in the embodiment shown in FIG. 3, comprises a wall or housing 24a which defines three openings—24b, 27 and 28, and a cavity 24c, and includes a tubular extension portion 24d. The opening 24b may be coaxial with the opening 28. The end 21b of the tube 21 may be forced fitted over a sleeve 21'', which itself is slipped over the tubular extension 24d, but only after the end 26 of the smaller inner tube 22 is first inserted through the opening 24b and passed through the cavity 24c and into a smaller receiving area 24e, into which the end 26 may be force fitted, thereby placing it in direct communication with the opening 28. After the end 26 of the inner tube 22 has thus been securely inserted in and gripped by the wall-defining the area 24e, and the outer tube end 21b has been attached over the tubular extension 24d in the manner heretofore described, the unilimb device of the present invention is ready for connection into a circle circuit system of the type shown in FIGS. 1 and 2, in the manner illustrated in FIG. 6. Thus, the opening 27 may be connected as at 14 in FIG. 2, and the opening 28 is connected to the inspiratory air line as at 13 in FIG. 2. The terminal element 23 then substitutes for the inlet-outlet 11 shown in FIGS. 1 and 2. Thereby, there are eliminated from the circuit the cumbersome double hose 9, 10, and Y-pipe connection shown at 11a in FIG. 1. The manner in which this substitution thus appears is illustrated in FIG. 6. While this device of the present invention in the embodiment illustrated in FIG. 3 provides a minimum of dead air space between the end 22' of inner tube 22 and the opening in the nozzle 23, which is connected to the inlet means (not shown) to the patient's respiratory system; should a small increase in such dead space be required or desireable in any situation, the same may be readily obtained by sliding the sleeve 21" axially to the left along the tubular extension 24d. Thereby, the corrugated outer tube 21 and terminal 23 are also displaced axially to the left relative to the inner tube 22, with the result that the end 22' becomes disposed toward the right further away from the opening in the nozzle end portion 23a of the terminal 23, to increase the dead space between said opening and end 22'.

It will be readily appreciated by those persons skilled in the art that the inspiratory air from the source 1, as supplemented by air from the carbon dioxide absorber 3, is brought to the inlet means (not shown) of the patient's respiratory system through the opening 28, the tube 22, and the terminal element 23. Expiratory air on the other hand, passes back from the patient into the terminal element 23, where it is diverted around the incoming inspiratory air at the end 22' of the inner tube 22, and into the passage of 21c between the outer corrugated tube 21 and the inner tube 22. This expiratory air is then brought back through the terminal element 24 via the passage defined by the tubular extension 24d, the cavity 24c, and the opening 27, from whence it is carried back past the reservoir bag 12, and into the carbon dioxide absorber 3 for reprocessing and ultimate return with fresh inspiratory gas.

Figure 5:
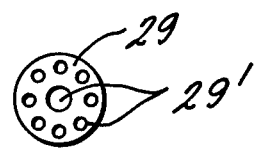
FIG. 5 is a front view of the transverse wall element 29 shown in FIG. 3.

It will be readily appreciated that in this particular embodiment shown in FIG. 3, there is provided in the terminal element 23, a minimum of dead space. While the device as illustrated in FIGS. 3-5 is to be preferred, at least for those applications where a minimum of dead space may be desired, other configurations of the terminal element and two tube ends may also be utilized.

Figure 7A:
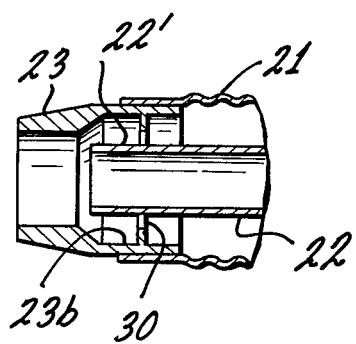
FIG. 7(a) is a longitudinal section of a modified form of the terminal element shown in the left-hand side of FIG. 3.
Figure 7B:
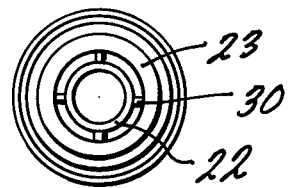
FIG. 7(b) is a front view of the modified transverse wall element 30 and surrounding elements shown in FIG. 7(a)

In the embodiment of the terminal element illustrated in FIGS. 7(a) and 7(b), the orificed transverse wall 29 of the FIG. 3 embodiment is omitted, and a plurality of radially extending spacers 30 secured to the cylindrical wall portion 23 are provided to support the end 22' of the tube 22 in coaxial alignment with the terminal element 23, and to limit the distance that the tube end 22' may extend toward the nozzle opening.

Figure 8A:
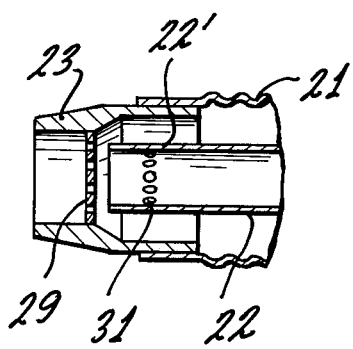
FIG. 8(a) is also a longitudinal section of the terminal element shown in the left-hand side of FIG. 3, but illustrating a modification in the end of the inner tube.
Figure 8B:
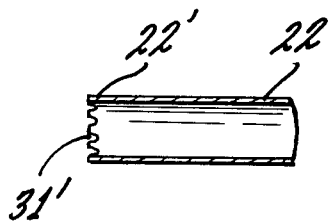
FIG. 8(b) is a longitudinal section of a still further modification of the end of the inner tube.

In the further embodiment of the terminal element illustrated in FIGS. 8(a) and 8(b), the only modifications over that of FIG. 3 lies in providing the orifices 31 or serrations 31' in the end 22' of the inner tubular member 22.

Figure 9A:
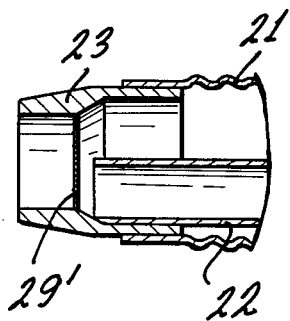
FIG. 9(a) is a longitudinal section of the terminal element shown on the left-hand side of FIG. 3, but illustrating the substitution for the transverse wall in FIG. 3 of a screen type wall, and a different disposition of the inner tube.
Figure 9B:
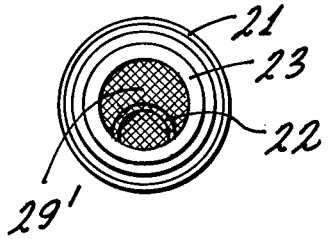

In the still further embodiment of the invention illustrated in FIGS. 9(a) and 9(b), there is substituted for the transverse wall 29 of the FIG. 3 embodiment, a screen-like member 29', and the inner inspiratory air tube is brought into the terminal element 23 along one side of the outer tubular member 21.

Figure 10A:
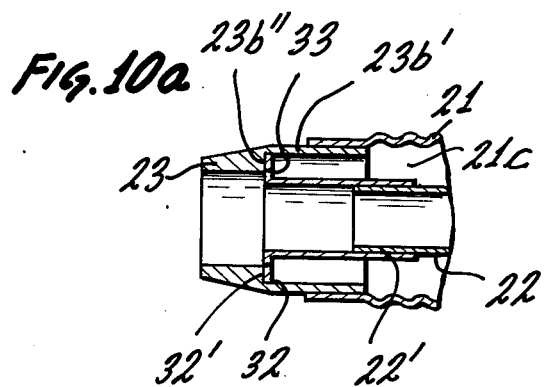
FIG. 10(a) is a longitudinal section of the terminal shown on the left-hand side of the FIG. 3, in a further modified form.
Figure 10B:
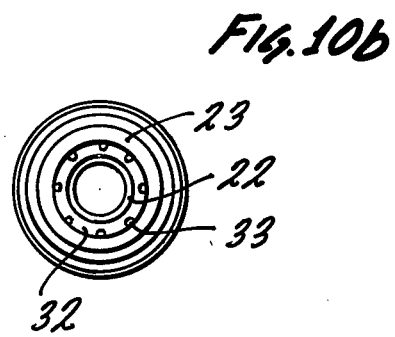
FIG. 10(b) is a view taken on the line aa of FIG. 10(a) looking in the direction of the arrows.

In the still further embodiment of the invention illustrated in FIGS. 10(a) and 10(b), there is substituted for the transverse wall 29 in the FIG. 3 embodiment, an orificed transverse annular wall 32', having a coaxial tubular extension 32 which serves to receive and limit the axial incursion of the end 22' of the inner tube 122. Additionally, the inner wall 23b' is configured to provide a counter bore type recess 23b'' to receive the radiating flange 32' which constitutes a transverse wall referred to above. This flange or wall 32' is punctured with a ring of orifices 33 for passage of expiratory air back into the passage 21c defined by the inner wall of the outer tube 21 and the outer wall of the inner tube 22.

Figure 11A:
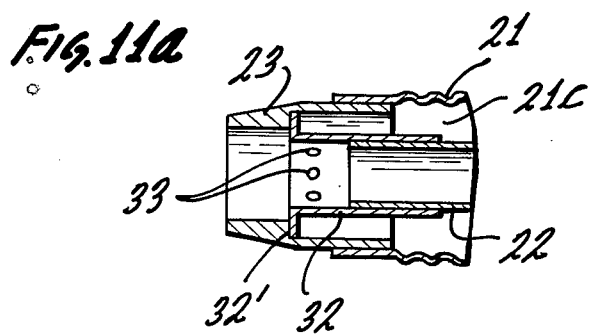
FIG. 11(a) is a longitudinal section of the terminal shown on the left-hand side of the FIG. 3 in a still further modified form.
Figure 11B:
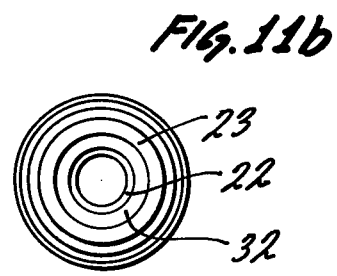
FIG. 11(b) is a view taken on the line a—a of FIG. 11a looking in the direction of the arrows.

In the last alternate embodiment of the terminal element 23, illustrated in FIGS. 11(a) and 11(b), it will be seen that this is quite similar in configuration to the embodiment of FIGS. 10(a) and 10(b), the difference being that the axially extending orifices 33, shown in FIGS. 10(a) and 10(b) have been eliminated from the transverse wall-flange 32. In place of said axially extending orifices 33, a series of orifices 33' have been provided in the tubular extension 32, thereby to permit the expiratory gas to pass into the passage 21c.

Figure 12:
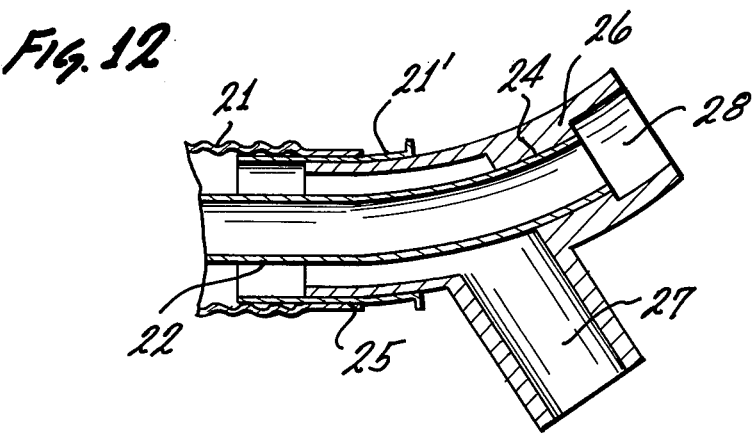
FIG. 12 is a longitudinal section of a modified form of the terminal shown on the right-hand side of FIG. 3.
Figure 13:
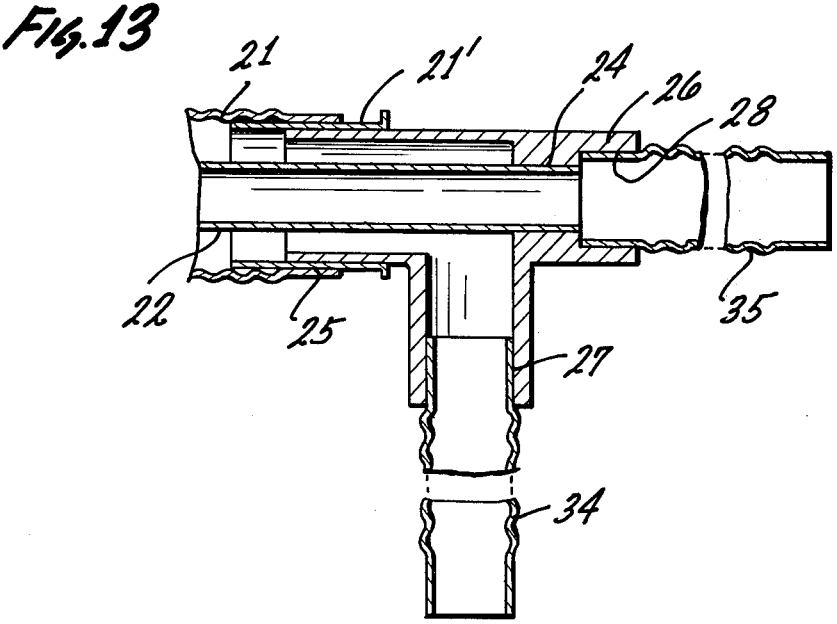
FIG. 13 is a longitudinal section of the terminal shown on the right-hand side of FIG. 3, but with base connections thereto.

FIG. 12 illustrates a possible different configuration for the right-hand terminal element shown in FIG. 3, and FIG. 13 illustrates the manner in which tubes 34 and 35 may be inserted into the openings 27 and 28 respectively, to place this element in communication with the carbon dioxide absorber 3 and the gas source 1 in a circuit such as illustrated in FIG. 6.

In the further embodiment of the invention illustrated in FIGS. 14 and 15, it will be noted that the basic device illustrated in FIG. 3 is employed, but it has been modified to the extent of having had its opening 27 closed by a plug 34', and instead of having the end of a connector tube 35 inserted into the opening 28, as illustrated in FIG. 13, an interfitting end 37 of an extension adapter 38 is pressed into the opening 28. This adapter, however, does not continue the separation of the inspiratory and expiratory air passages in the manner accomplished by the terminal element 24, as illustrated in FIGS. 3, 12 and 13. Instead, the extension adapter 38 defines a single cavity 39, into which there are three openings 40, 41, and 42. Opening 40 is placed in direct communication with the inner tube 22. The oppositely disposed opening 41 is placed in communication with the tube 35 from the source of gas 1 and reprocessed gas from the $CO_2$ absorber 3; while the third opening 42 is placed in communication through the elbow 43 and the hose 36 with the carbon dioxide absorber 3, in the manner shown in the schematic diagram of FIG. 15. This adaptation of the present invention, in effect, provides an extensive dead space for use in situations where it is desired to increase the level of carbon dioxide in the patient's respiratory system.

Figure 16:
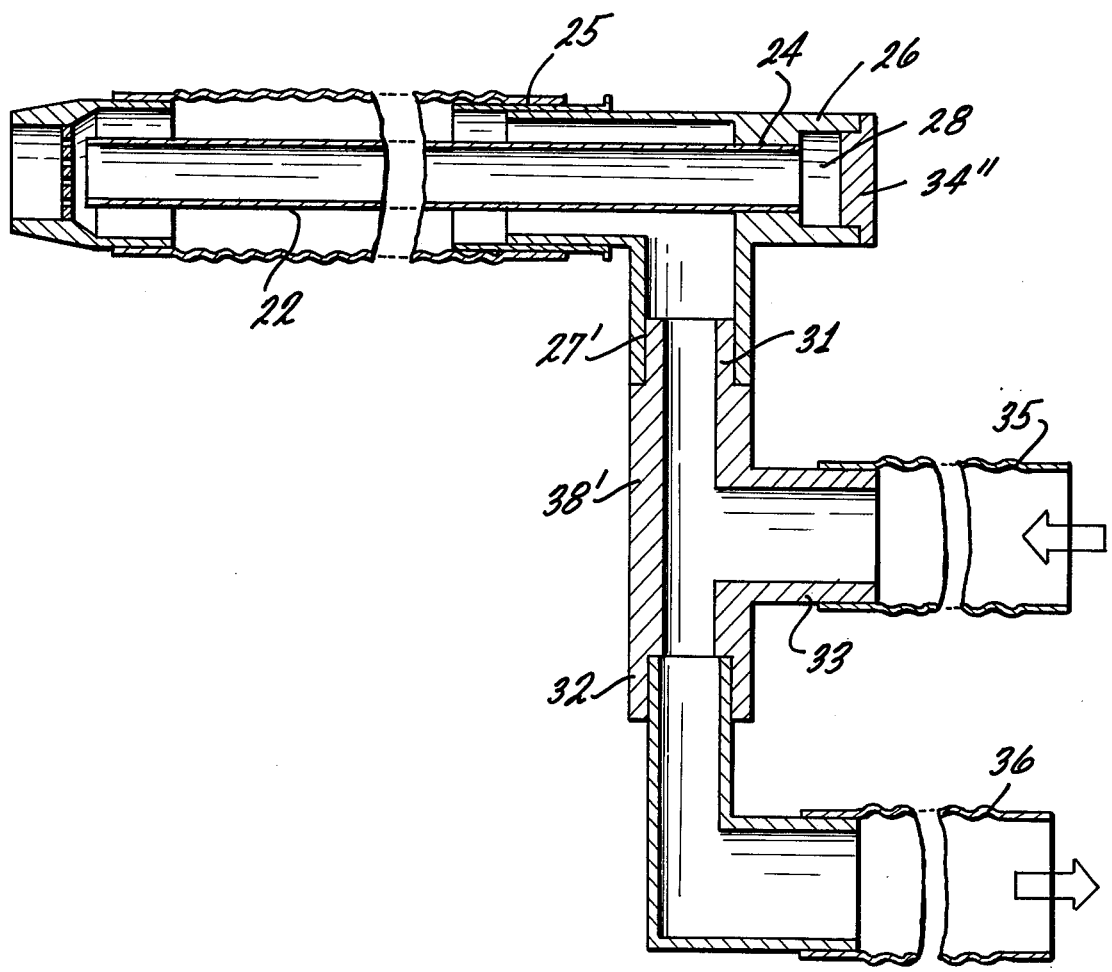
FIG. 16 is a sectional-view of still further modification of, and addition to, the terminal illustrated on the right-hand side of FIG. 3.

In the further adaptation illustrated in FIG. 16, the plug 34" serves to close off the opening 28 and hence, the end of the inner tube 22. The circle circuit illustrated in FIG. 16, in this alternative embodiment, is connected by the adapter 38' to the opening 27' and the two hoses 35 and 36. By this adaptive embodiment, it may be seen that the circle circuit is provided with more extensive dead space by employing only the outer tube 21 not the inner tube 22.

From the foregoing it will be readily appreciated by those skilled in the art that the device of the present invention may not only be employed effectively in a circle circuit breathing system to provide a minimum of dead space but is may be readily adapted to provide greatly augmented dead space in such a system, and also may be adapted for use in various other presently known breathing systems. The device may be readily assembled from its basic components and, since it contains no moving valve parts, it is completely safe and reliable. Because of the simplicity of the structure of its components, it is easy to dissassemble for cleaning and sterilization. Moreover, since its components may be inexpensively manufactured, any of such components, or even the entire device may be disposed of after usage in certain situations, without great economic loss.

What is claimed is:

1. A unilimb device for use in a breathing circuit wherein inspiratory gas from a source thereof is delivered through inlet means to a person's respiratory system, and expiratory gas exhaled by the person passes back through said inlet means, said device comprising:

A. first flexible tube means of such internal diameter as to pass the required volume of gas at the required rate from the source thereof to said inlet means to provide inspiration for the person, and said first flexible tube having a predetermined external diameter;

B. second flexible tube means enclosing most of the length of the first flexible tube, means said second flexible tube means being of such internal diameter greater than the predetermined external diameter of the first flexible tube means as to provide a sufficient cross-sectional area of passage between the first flexible tube means and the enclosing second flexible tube means to pass expiratory gas from the person at the required rate;

C. first terminal element means, said first terminal element means being generally tubular in configuration, short in length, and having one open nozzle end for communication with said inlet means, and an opposite open end including means for receiving and gripping a first end of the second flexible tube means and to dispose it close to the open nozzle end; said first terminal element means having a tubular wall defining a passage therethrough, a first end of the first flexible tube means being unattached to said second flexible tube means amd said first terminel element means and extending axially toward said open nozzle end, and means within said first terminal element means for limiting the axial extension of said first end of the first flexible tube means toward said open nozzle end, to provide a passage for expired first end of said flexible tube means said open nozzle and said gas passage;

D. second terminal element means comprising a wall defining a cavity and first, second and third openings to said cavity, said second terminal element means having a tubular extension defining said first opening including means for receiving and gripping the second end of the second end of the second flexible tube means, said tubular extension defining said first opening having an inner diameter larger than the outer diameter of said first flexible tube means;

said second opening being disposed opposite said first opening, said second opening including means for receiving and securely gripping the second end of the first flexible tube means, when said first flexible tube is inserted through said first opening, through said cavity into said receiving and gripping means thereby placing said first tubular means in direct communication with said second opening;

said third opening communicating with said cavity thereby placing said third opening in communication with said second flexible tube means through said cavity and said first opening.

2. The device as defined in claim 1 wherein said means for limiting the axial extension of the first flexible tube means comprises a transverse, orificed wall proximate the open nozzle end.

3. The device as described in claim 1 wherein the first end of the first flexible tube means is orificed radially to provide gas passages directly between the end area of the first flexible tube means and the gas passage about said first flexible tube means end and defined by the inner wall of said first terminal element means.

4. The device as described in claim 2 wherein the orificed transverse wall is comprised of screening.

5. The device as described in claim 1, wherein the axes of the second and third openings in the second terminal element means intersect each other at other than a right angle.

6. In combination with the device as described in claim 1, means to plug the second opening in the second terminal element means thereby to close off the second end of the first flexible tube means, and adapter means, said adapter means having one end interfittable into the third opening in the second terminal element means, said adapter means defining a gas passage extending from its said one end and two further openings to the last said gas passage, each of said openings being connectible to conduits in a breathing circuit.

7. In combination with the device as described in claim 1, means to plug the third opening in said second terminal element means thereby to close the same to any gas passage therethrough, and adapter means, said adapter means having one end interfittable into the second opening in the second terminal element means, said adapter means defining a gas passage extending from its said one end and two further openings to the last said gas passage, each of said openings being connectible to conduits in a breathing circuit.

8. The device as described in claim 1 wherein sleevelike means are interposed radially between the tubular extension of the second terminal element means and the second end of the second flexible tube means, the last said end being fixedly fitted about a portion of said sleevelike means and the latter being axially slidable relative to said tubular extension.

9. The device as described in claim 1 wherein sleevelike means are interposed radially between the tubular extension of the second terminal element means and the second end of the second flexible tube means, the last said end being fixedly fitted about a portion of said sleevelike means, and the latter being rotatable relative to said tubular extension.

* * * * *

UNITED STATES PATENT AND TRADEMARK OFFICE
CERTIFICATE OF CORRECTION

PATENT NO. : 4,265,235
DATED : May 5, 1981
INVENTOR(S) : Atsuo F. Fukunaga

It is certified that error appears in the above-identified patent and that said Letters Patent are hereby corrected as shown below:

In the drawings, Sheets 6, 7 and 8, Figs. 12, 13, 14. and 16, the reference numeral 24 should be applied to the element whose reference numeral appears as 26; the reference numeral 26 should be applied to the element whose reference numeral appears as 24. Column 7, line 63, that portion reading "tube 122". should read -- tube 22 --. Column 9, line 16, that portion reading "flexible tube, means said" should read -- flexible tube means, said --. Column 9, lines 34 to 35, that portion reading "means amd said first terminel" should read -- means and said first terminal --. Column 9, lines 40 to 41, that portion reading "a passage for expired first end of said flexible tube means said open nozzle and said gas passage;" should read -- a passage for expired gas between said open nozzle and said first end of said first flexible tube means; --. Column 9, lines 47 to 48, that portion reading "second end of the second end of the second flexible tube" should read -- second end of the second flexible tube --. Column 9, line 56, that portion reading "tube is inserted" should read -- tube means is inserted --.

Signed and Sealed this

Third Day of November 1981

[SEAL]

Attest:

GERALD J. MOSSINGHOFF

Attesting Officer

Commissioner of Patents and Trademarks